United States Patent [19]

Fujita et al.

[11] Patent Number: 5,436,133
[45] Date of Patent: Jul. 25, 1995

[54] ENZYME ASSAY OF BIOCHEMICAL SUBSTANCES

[75] Inventors: Tuyosi Fujita, Osaka; Isamu Takagahara, Hyogo, both of Japan

[73] Assignee: Oriental Yeast Co., Ltd., Tokyo, Japan

[21] Appl. No.: 865,715

[22] Filed: Apr. 8, 1992

Related U.S. Application Data

[63] Continuation of Ser. No. 381,719, filed as PCT/JP88/00881, Sep. 2, 1988

[51] Int. Cl.⁶ .............. C12Q 1/32; C12Q 1/28; G01N 33/50; G01N 33/52
[52] U.S. Cl. .............. 435/26; 435/28; 435/962; 436/8; 436/34; 436/825
[58] Field of Search .............. 435/26, 28, 962; 436/8, 436/34, 825

[56] References Cited

U.S. PATENT DOCUMENTS

| | | | |
|---|---|---|---|
| 3,864,085 | 2/1975 | Woodbridge | 436/86 |
| 4,657,856 | 4/1987 | Terada et al. | 435/28 |
| 4,742,001 | 5/1988 | Marui et al. | 435/26 |
| 4,855,228 | 8/1989 | Charlton et al. | 435/28 |
| 5,162,201 | 11/1992 | Imamura et al. | 435/19 |

FOREIGN PATENT DOCUMENTS

| | | | |
|---|---|---|---|
| 0124909 | 11/1984 | European Pat. Off. | C12Q 1/32 |
| 0207493 | 1/1987 | European Pat. Off. | C12Q 1/32 |
| 57-29159 | 6/1982 | Japan . | |
| 61-173790 | 8/1986 | Japan . | |
| 61-173799 | 8/1986 | Japan . | |

OTHER PUBLICATIONS

Nihon Nogei Kagakukai-hen [Nihon Nogei Kagakukai ABC Series (4) Koso-Biotechnology end Shishin-I], 20 Mar. 1985, Asakura Shoten (Tokyo) pp. 94–114.
Ranpakushitsu Kakusan Toso Rinji Zokan-Go (Glutathione Kenkyu no Epoch), vol. 33 (9), Jul. 1988 (Tokyo) Takahashi Kazuhiko [Selenium to Glutathioneperoxidase] pp. 1495–1504.
Mahler et al., "Basic Biological Chemistry", Harper & Row, Pubs., Inc., N.Y., N.Y. pp. 202, 327 & 328 (1968).
Heath et al., Anal. Biochem. 76:184–191 (1976).
Mahler et al., *Basic Biological Chemistry*, Harper & Row, Publ., Inc., N.Y., pp. 357–358 (1966).
Oriental Yeast Catalog, pp. 49, 50, 59–62 (1987).
Tijssen, P., *Practice and Theory of Enzyme Immunoassays* (Elsevier, N.Y.) pp. 186–187 (1985).

*Primary Examiner*—Michael P. Woodward
*Attorney, Agent, or Firm*—Browdy & Neimark

[57] ABSTRACT

This invention relates to an enzyme assay for quantitative analysis of biochemical substances using NAD(P)-NAD(P)H system and utilizing hydrogen peroxide, in which isocitric acid, metal ions and isocitrate dehydrogenase are previously added to a test sample, thereby consuming the endogenous substances that interfere the analysis, and at the same time regenerating NAD(P)H reduced.

The isocitrate dehydrogenase is then inactivated by addition of a chelating agent, an enzyme or substrate that generates hydrogen peroxide as reaction product is added simultaneously or thereafter, and the amount of hydrogen peroxide thus formed is measured.

Biochemical substances that generate hydrogen peroxide as reaction product can be correctly analyzed by this method with no adverse effect of endogenous substances because these interfering substances have been removed prior to measurement.

10 Claims, No Drawings

ENZYME ASSAY OF BIOCHEMICAL SUBSTANCES

This application is a continuation of application Ser. No. 07/381,719, filed Jun. 20, 1989, which was the national stage of PCT application Ser. No. PCT/JP88/00881, filed on Sep. 2, 1988.

FIELD OF THE INVENTION

This invention relates to an enzyme assay of biochemical substances. More particularly, it relates to an enzyme assay for the content of hydrogen peroxide ($H_2O_2$)—a method of analyzing substances contained in body fluid (e.g., blood and urine) or biochemical substances generating $H_2O_2$ as a result of biochemical reaction. The amounts of a variety of precursors participating in the formation of $H_2O_2$ contained in a test sample can be determined by the method of this invention. Thus, this invention includes the quantitative analysis of such precursors and related enzymes by treating the precursors with an oxidase and measuring the amount of $H_2O_2$ thus formed.

PRIOR ART

In the conventional substrate or enzyme analysis using $H_2O_2$ in the detection system, a known technique to measure the amount of $H_2O_2$ is to allow a hydrogen donor to react with an electron or radical receptor (coupler) in the presence of a peroxidase (oxidative condensation) to form a colored substance by the action of $H_2O_2$, followed by colorimetry. As examples of the hydrogen donor, there may be mentioned dimethylaniline, diethylaniline, o-tolidine, o-toluidine, p-toluidine, o-phenylenediamine, N-ethyl-N-(3-methylphenyl-N'-succinylethylenediamine), N,N'-diemthyl-p-phenylenediamine, benzidine, o-diánisidine, p-anisidine, dianisidine, o-cresol, p-chlorophenol, N,N-diethyl-m-toluidine, N-ethyl-N-(2-hydroxy-3-sulfopropyl)-m-toluidine sodium (TOOS), m-cresol, α-naphthol, β-naphthol, catechol, guaiacol, pyrogallol, 2,7-diaminofluorene, N-ethyl-N-(3-methylphenyl)-N'-acetylethylenediamine, leucoindophenol, 2,4-dichlorophenol and 2-hydroxy-3,5-dichlorobenzenesulfonic acid. Illustrative examples of the coupler include 2-thiophenecarboxylic acid hydrazine, benzidine, 3-methyl-2-benzothiazolinone hydrazone and 4-aminoantipysine.

As the peroxide activator, may be used, besides peroxidase, tungstic acid, a salt thereof, molybdic acid, a salt thereof, a mixture of one of these inorganic compounds with iodide.

This method, however, has the disadvantages that the sensitivity is low, the reagents used evolve disagreeable odor and are low in stability, the color to be measured is liable to be affected by hemoglobin, bilirubin and other pigment contained in test samples, and consistent data cannot be obtained when the blanks for reagent fluctuate because this method is based on relative measurment.

Another type of method is also known, in which $H_2O_2$ is allowed to react with ethanol or methanol by the action of a catalase, and the amount of acetaldehyde or formaldehyde formed is determined by adding acetaldehyde dehydrogenase or formaldehyde dehydrogenase and measuring the increased amount of AND(P)H.

But correct analysis of acetaldehyde is difficult with test samples from drinkers who take much alcoholic beverages because of a lot of acetaldehyde contained in the blood and urine. To avoid such effects of endogenous substances, the following techniques have been proposed and put into practice.

In the first technique, a catalase is used in the elimination step, it is inactivated by addition of sodium azide at the end of elimination, and an enzyme or substrate that generates $H_2O_2$ after reaction is then added, followed by colorimetry by the use of a peroxidase (POD) color-development system. The problems involved in this technique are that whether or not sodium azide is able to completely inactivate the catalase is uncertain and that oxidase in general (including POD) has inhibitory action.

In the second technique, an oxidase is allowed to act directly, or indirectly in the presence of other type of enzyme or substrate, upon the endogenous substance in question, $H_2O_2$ thus formed is condensed with a hydrogen donor in the presence of POD to produce an inactive compound having no absorption in the visible region, thereby eliminating the endogenous substance, and thereafter measurement is started (Japanese Patent Publication No.29159/1982).

Actually, however, the condensation product generally shows slight absorption in the visible region, causing positive errors particularly when measuring a small amount of body-fluid substances.

In the third technique (as disclosed in Japanese Patent Kokai No.1737/1986), a catalase is used in an amount less than ten times that of POD, thus eliminating the need for the use of sodium azide. In this case, however, measurement is started without inactivating the catalase used, and hence decomposition of $H_2O_2$ by the catalase during measurement is unavoidable, thus causing negative errors.

Thus, any of the techniques described above involves some problems.

PROBLEMS TO BE SOLVED

As stated above, the peroxidase method has the disadvantages of low sensitivity and incorrect measurement, while the catalase method suffers from the adverse effects of endogenous substances and the techniques so far proposed to eliminate such endogenous substances give no satisfactory result.

MEANS TO SOLVE THE PROBLEMS

This invention was intended to develop a novel method for the quantitative analysis of biochemical substances which uses $H_2O_2$ as reaction product and is free from the problems mentioned above. To be more specific, this invention was intended to develop a new enzyme assay under the notion that absorbance measurement in the ultraviolet region would be the best in order to meet the general demand for an analytical method which can be simply performed without diluting test samples, is not adversely affected by any other substances, and can be applied to automatic analyzers.

This invention was accomplished as a result of intensive studies over a wide range of scientific fields, such as enzyme assay, enzymology, biochemistry and analytical chemistry. Thus, this invention relates to a method of measuring the amount of an enzyme or a substrate using $H_2O_2$ in the detection system, which comprises adding all the required enzymes or enzyme groups, or all the required substrates or substrate groups, to the detection system, allowing oxidase to act upon the reaction products to form $H_2O_2$, oxidizing reduced-form glutathione (GSH) into its oxidized form (GSSG) by the action of GSHPOD in the presence of $H_2O_2$, converting NADPH or NADH into AND+ or NADP+ by the action of GSH reductase (GR), and measuring the change in absorbance in the ultraviolet region, thereby determining the amount of substrate or enzyme, wherein the endogenous substances contained in the test sample that participate in the measurement system and cause measurement errors are previously consumed by the coupled reaction with isocitric acid, metal ions and isocitrate dehydrogenase (iCDH), a metal chelating agent is added at the end of elimination to completely terminate the iCDH reaction, simultaneously or thereafter an enzyme or substrate that generates $H_2O_2$ as final reaction product is added, and the amount of $H_2O_2$ thus formed is measured without adverse effect of any other substances. Described below is the method of this invention in more detail.

The method of this invention consists of two reaction systems. The first one is the $H_2O_2$ detection system, which may be expressed by the following formula (1):

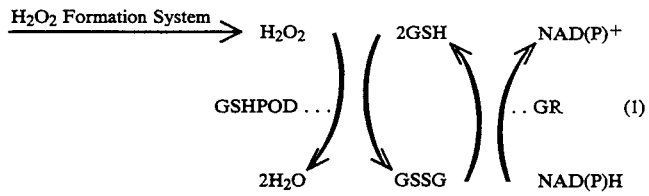

Hydrogen peroxide is allowed to react with a sufficient amount of GSH in the presence of GSHPOD, GSSG thus formed is reduced by GR, and the resultant decrease in the amount of AND(P)H is determined by measurement of absorbance at 340 nm. Thus, the method of this invention, in which the decrease in absorbance caused by the consumption of AND(P)H is measured, assures correct measurement because of no adverse effects of colored substances in test samples and because of the known molar extinction coefficient. In addition, the effect of reducing substances, such as cystein, GSH and ascorbic acid, is minimized because of the sufficient amount of GSH present in the system.

The second reaction system to eliminate the endogenous substances contained in body fluid (elimination system) is represented by the following formula (2):

allylamine for monoamine oxidase; hypoxanthine for inorganic phosphorus; oxaloacetic and pyruvic acids for transaminase; N-acetylneuraminic and pyruvic acids for sialic acid; xanthine for guanase; and $\beta$-glucose for $\alpha$-glucose. Hydrogen peroxide derived from these endogenous substances is eliminated by GSHPOD and GR; AND(P)H thus consumed is regenerated by the coupled reaction of isocitric acid, iCDH and metal ions (e.g., magnesium and manganese ions), and; iCDH is inactivated by a chelating agent, thereby completely terminating the reaction from AND(P)+into AND(F)H. Simultaneously or thereafter an enzyme or substrate that generates $H_2O_2$ as final reaction product is then added, and the amount of $H_2O_2$ thus formed is accurately measured without adverse effect of any other substances, the present invention's characteristic existing in this advantage. Furthermore, superoxide dismutase may also be added to the measurement system of this invention.

The metal ions herein include ions of magnesium, manganese, iron, copper, zinc, tin, and calcium.

The chelating agent includes EDTA and salts thereof, 1,2-bis(o-aminophenoxy)ethane-N,N,N',N'-tetraacetic acid and salts thereof, 1,3-diaminopropan-2-ol-N,N,N',N'-tetraacetic acid and salts thereof, diethylenetriamine-N,N,N',N'',N''-penaaetic acid and salts thereof, diethylenediamine-di-o-hydroxyphenylacetic acid and salts thereof, ethylenediamine-N,N'-diacetic acid and salts thereof, ethylenediamine-N,N'-dipropionic acid and salts thereof, N-hydroxyethylethylenediamine-N,N',N'-triacetic acid and salts thereof, ethylenediaminete-N,N,N',N'-trakis(methylenephosphonic acid). and salts thereof, glycoletherdiamine-N,N,N'-tetraacetic acid and salts thereof, hydroxyethyliminodiacetic acid and salts thereof, iminodiacetic acid and salts thereof, 1,2-diaminopropane-N,N,N',N'-tetraacetic acid and salts thereof, nitrilotriacetic acid

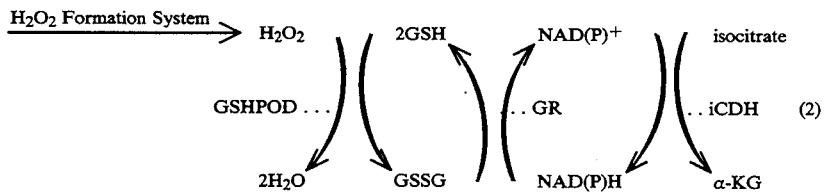

(wherein $\alpha$-KG: $\alpha$-ketoglutaric acid)

Test samples (such as serum and urine) generally contain, substances which participate in the reaction system to analyze the biochemical substance being measured (such as enzyme and substrate), thus producing measurement errors. These include free glycerol and glycerol 3-phosphate for triglyceride; creatine and sarcosine for creatinine; sarcosine for creatine; free cholesterol for cholesterol esters; choline for phospholipids, such as lecithin, lysolecithin and sphingomyelin; acetyl-CoA for free fatty acids; choline and o-toluoylcholine for choline esterase; maltose and glucose for amylase;

and salts thereof, nitrilotripropionic acid and salts thereof, nitrilotris(methylenephosphonic acid) and salts thereof, and triethylenetetramine-N,N,N',N'',N''',N'''-hexaacetic acid and salts thereof.

Listed below are typical examples of the $H_2O_2$ formation systems used in the method of invention for the quantitative analysis of substrates and enzymes, which are offered by way of illustration and not by way of limitation.

(1)

$$\text{Cholesterol} + \text{H}_2\text{O} \xrightarrow{\text{Cholesterol esterase}} \text{Free cholesterol} + \text{Fatty acid ester}$$

$$\text{Free cholesterol} + \text{O}_2 \xrightarrow{\text{Cholesterol oxidase}} \Delta^4\text{-Cholestenone} + \text{H}_2\text{O}_2$$

(2)

$$\begin{bmatrix}\text{Lecithin, Lysolecithin,} \\ \text{Sphingomyelin}\end{bmatrix} \xrightarrow{\text{Phospholipase}}$$

$$\text{Choline} \xrightarrow{\text{Choline oxidase}} \text{Betaine} + 2\text{H}_2\text{O}_2$$

(3)

$$\text{Neutral fat} + \text{H}_2\text{O} \xrightarrow{\text{Lipoprotein lipase}} \text{Glycerol} + \text{Fatty acid}$$

$$\text{Glycerol} + \text{O}_2 \xrightarrow{\text{Glycerol oxidase}} \text{Glyceraldehyde} + \text{H}_2\text{O}_2$$

(4)

$$\text{Neutral fat} + \text{H}_2\text{O} \xrightarrow{\text{Lipoprotein lipase}} \text{Glycerol} + \text{Fatty acid}$$

$$\text{Glycerol} + \text{ATP} \xrightarrow{\text{Glycerol kinase}} \text{Glycerol-3-phosphate} + \text{ADP}$$

$$\text{Glycerol-3-phosphate} \xrightarrow{\text{Glycerol-3-phosphate oxidase}} \text{Dihydroxyacetone phosphate} + \text{H}_2\text{O}_2$$

(5)

$$\text{RCOOH} + \text{ATP} + \text{CoA} \xrightarrow{\text{Acy-CoA synthetase}} \text{Acyl-CoA} + \text{AMP} + \text{PPi}$$

$$\text{Acyl-CoA} + \text{O}_2 \xrightarrow{\text{Acy-CoA oxidase}} \text{2,3-Trans-enoyl-CoA} + \text{H}_2\text{O}_2$$

(6)

$$\text{Uric acid} + \text{O}_2 + \text{H}_2\text{O} \xrightarrow{\text{Uricase}} \text{Allantoin} + \text{CO}_2 + \text{H}_2\text{O}_2$$

(7)

$$\text{D-Gluconic acid} + \text{O}_2 \xrightarrow{\text{Glucose oxidase}} \text{D-Glucosone} + \text{H}_2\text{O}_2$$

(8)

$$\text{o-Toluoylcholine} + \text{H}_2\text{O} \xrightarrow{\text{Choline esterase}} \text{o-Toluylic acid} + \text{Choline}$$

$$\text{Choline} + \text{O}_2 \xrightarrow{\text{Choline oxidase}} \text{Betaine} + 2\text{H}_2\text{O}_2$$

(9)

$$\text{Maltopentaose} \xrightarrow{\text{Amylase}} \text{Maltotriose} + \text{Maltose}$$

-continued $$\text{Maltose} + \text{Pi} \xrightarrow{\text{Maltose phosphorylase}} \text{Glucose} + \beta\text{-Glucose-1-phosphate}$$

$$\text{Glucose} + \text{O}_2 \xrightarrow{\text{Glucose oxidase}} \text{Gluconic acid} + \text{H}_2\text{O}_2$$

(10)

$$\text{CH}_2=\text{CHCH}_2\text{NH}_2 + \text{O}_2 + \text{H}_2\text{O} \xrightarrow{\text{Monoamine oxidase}}$$

$$\text{CH}_2=\text{CHCHO} + \text{NH}_3 + \text{H}_2\text{O}_2$$

(11)

$$\text{H}_3\text{PO}_4 + \text{Inosine} \xrightarrow{\text{Purine nucleoside phosphorylase}} \text{Hypoxanthine} + \text{Ribose-1-phosphate}$$

$$\text{Hypoxanthine} + 2\text{O}_2 + 2\text{H}_2\text{O} \xrightarrow{\text{Xanthine oxidase}} \text{Uric acid} + 2\text{H}_2\text{O}_2$$

(12)

$$\text{Pyruvic acid} + \text{O}_2 + \text{Pi} \xrightarrow{\text{Pyruvate oxidase}} \text{Acetylphosphoric acid} + \text{CO}_2 + \text{H}_2\text{O}_2$$

(13)

$$\text{L-Lactic acid} + \text{O}_2 \xrightarrow{\text{Lactate oxidase}} \text{Pyruvic acid} + \text{H}_2\text{O}_2$$

(14)

$$\text{L-Aspartic acid} + \alpha\text{-Ketoglutaric acid} \xrightarrow{\text{Glutamic-oxaloacetic transaminase}} \text{Oxaloacetic acid} + \text{L-Glutamic acid}$$

$$\text{Oxaloacetic acid} \xrightarrow{\text{Oxaloacetate decarboxylase}} \text{Pyruvic acid} + \text{CO}_2$$

$$\text{Pyruvic acid} + \text{O}_2 + \text{Pi} \xrightarrow{\text{Pyruvate oxidase}} \text{Acetylphosphoric acid} + \text{CO}_2 + \text{H}_2\text{O}_2$$

(15)

$$\text{L-Alanine} + \alpha\text{-Ketoglutaric acid} \xrightarrow{\text{Glutamic-pyruvic transaminase}} \text{Pyruvic acid} + \text{L-Glutamic acid}$$

$$\text{Pyruvic acid} + \text{O}_2 + \text{Pi} \xrightarrow{\text{Pyruvate oxidase}} \text{Acetylphosphoric acid} + \text{CO}_2 + \text{H}_2\text{O}_2$$

(16)

$$\alpha\text{-Glucose} \xrightarrow{\text{Mutarotase}} \beta\text{-Glucose}$$

$$\beta\text{-Glucose} + \text{O}_2 \xrightarrow{\text{Glucose oxidase}} \text{Gluconic acid} + \text{H}_2\text{O}_2$$

(17)

$$\text{Creatine} + \text{H}_2\text{O} \xrightarrow{\text{Creatinine amidohydrolase}} \text{Creatine}$$

-continued

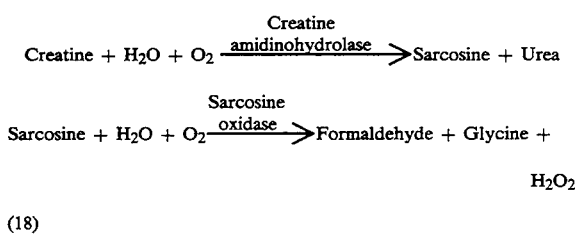

(18)

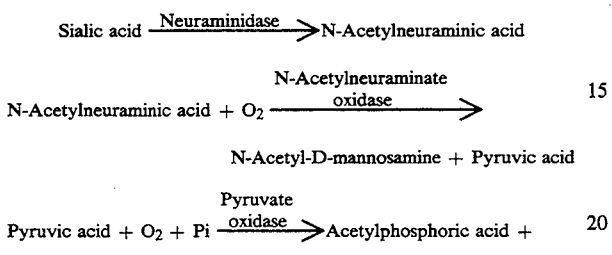

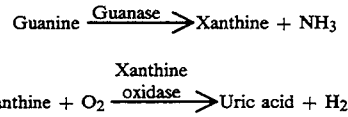

$$Guanine \xrightarrow{Guanase} Xanthine + NH_3$$

$$Xanthine + O_2 \xrightarrow{Xanthine\ oxidase} Uric\ acid + H_2O_2$$

The following examples will further illustrate the invention.

Example 1

To 1.5 ml of 0.1M K-PO$_4$ solution (pH 7.5) containing 0.6 mM oxonic acid, 2 mM GSH, 0.5 mM NADPH, 2 mM NAN$_3$, 0.5 u/ml GR, 1 u/ml GSHPOD, 1 u/ml iCDH, 5 mM isocitric acid and 0.2 mM MgCl$_2$, was added 75 µl each of serial dilutions of 120 mg/dl uric acid solution (test samples), and the mixture was allowed to stand at 37° C. for three to five minutes. 0.1M K-PO$_4$ solution (pH 7.5) containing 9 u/ml uricase and 20 mM EDTA-4 Na was then added (1.5 ml each), the reaction was allowed to proceed at 37° C., and the decrease in absorbance at 340 nm was measured over a period of three minutes. The change in absorbance per minute ($\Delta A_{340nm}/min$) was calculated from the data in the part of high linearity. The result is summarized in the table below.

|  | Sample No. | | | | | |
|---|---|---|---|---|---|---|
|  | 1 | 2 | 3 | 4 | 5 | 6 |
| Uric acid (mg/dl) | 0 | 24 | 48 | 72 | 96 | 120 |
| Measurements ($\Delta A_{340\ nm}$/min) | 0.0020 | 0.0415 | 0.0760 | 0.1190 | 0.1567 | 0.1822 |

As can be seen from the table, a linear relationship was obtained at uric acid concentrations up to 120 mg/dl at a sample: reagent ratio of 1:40.

Example 2

To 1.5 ml of 0.1M potassium phosphate buffer solution (pH 7.0) containing 2 mM GSH, 0.5 mM NADPH, 2 mM NAN$_3$, 0.5 u/ml GR, 2 u/ml iCDH, 10 mM isocitric acid, 1 u/ml GSHPOD and 0.2 mM MgCl$_2$, was added 20 µl each of serial dilutions (0 to 300 mg/dl) of aqueous cholesterol solution, and the mixture was allowed to stand at 37° C. for five minutes. 0.1M potassium phosphate buffer solution (pH 7.0) containing 20 mM EDTA-4Na and 6 u/ml cholesterol oxidase was then added (1.5 ml each), the mixture was allowed to stand at 37° C. for 15 minutes and then at room temperature for about ten minutes, and the absorbance at 340 nm was measured. The result obtained is summarized in the table below.

|  | Sample No. | | | | | |
|---|---|---|---|---|---|---|
|  | 1 | 2 | 3 | 4 | 5 | 6 |
| Cholesterol (mg/dl) | 0 | 60 | 120 | 180 | 240 | 300 |
| Measurements ($\Delta A_{340\ nm}$/min) | 0.002 | 0.062 | 0.130 | 0.195 | 0.249 | 0.312 |
| (mg/dl) | 0 | 57 | 121 | 182 | 233 | 292 |

As can be seen from the table, the amounts of cholesterol in test samples could be measured with high linearity at a sample: reagent ratio of 1:150.

The following equation was used for the calculation of cholesterol concentration:

$$mg/dl = \frac{\Delta A \times 3.02}{6.2 \times 0.02} \times \frac{386.64}{1000} \times 100$$

wherein $\Delta A = A - A_0$ ($A_0$ is reagent blanks, for which Sample No. 1 is allotted)

6.2 = Absorbance of 1 mM NADPH 3.02 = Total volume of reaction system (ml)

0.02 = Volume of test sample (ml)

386.64 = Molecular weight of cholesterol

Example 3

To 2 ml of a reaction mixture obtained from 5 u/ml maltose phosphorylase, 10 u/ml glucose oxidase, 0.2 mM MgCl$_2$, 1.5 mM GSH, 0.38 mM NADPH, 0.75 u/ml GR, 1.5 u/ml GSHPOD, 1.5 u/ml iCDH, 7.5 mM isocitric acid and 0.1M phosphate buffer solution (pH 7.2), was added 50 µl each of patients serum samples of known amylase activity (152 u/l for Sample A, 329 u/l for Sample B, 192 u/l for Sample C, 211 u/l for Sample D and 436 u/l for Sample E), and the mixture was allowed to stand at 37° C. for three to five minutes. 0.1M phosphate buffer solution (pH 7.2) containing 0.03 mM maltopentaose and 30 mM EDTA was then added (1 ml each), the reaction was allowed to proceed at 37° C., and the change in absorbance at 340 nm per minute was measured. The result obtained is summarized in the table below.

|  | Sample No. | | | | |
|---|---|---|---|---|---|
|  | A | B | C | D | E |
| Amylase activity (u/l) | 152 | 329 | 192 | 211 | 436 |
| Measurements ($\Delta A_{340\ nm}$/min) | 0.015 | 0.035 | 0.020 | 0.021 | 0.045 |
| Activity (u/l) | 148 | 344 | 197 | 207 | 443 |

The following equation was used for the calculation of amylase activity:

$$u/l = \frac{\Delta A_{340nm}/min \times 3.05}{6.2 \times 0.05} \times 1000$$

wherein
3.05: Final volume of reaction system (ml)
0.05: Volume of test sample (ml)
6.2: Molar extinction coefficient of NADPH (mM)

Example 4

To 1 ml of 0.1M phosphate buffer solution (pH 7.8) containing 20 u/ml creatine amidinohydrolase, 0.5 u/ml sarcosine oxidase, 2 mM GSH, 0.4 mM NADPH, 0.5 u/ml GR, 1 u/ml GSHPOD, 2 u/ml iCDH, 5 mM isocitric acid and 0.2 mM MgCl$_2$, was added 20 µl each of serial dilutions of aqueous creatinine solution (0 to 100 mg/dl), and the mixture was allowed to stand at 37° C. for five minutes. 0.1M phosphate buffer solution (pH 7.8) containing 20 mM EDTA-4Na and 32 u/ml creatinine amidohydrolase was then added (1 ml each), the reaction was allowed to proceed at 37° C., the change in absorbance at 340 nm was measured from two minutes after the start of reaction over a period of 30 seconds, and the change per minute was calculated. The result obtained is summarized in the table below.

| Dilution (mg/dl) | 0 | 20 | 40 | 60 | 80 | 100 |
|---|---|---|---|---|---|---|
| Measurements: $\Delta A_{340}$ nm/min (mAbs) | 0.1 | 39.2 | 72.6 | 111.3 | 124.9 | 169.9 |

As can be seen from the table, a good linear relationship was observed.

Example 5

Test samples of concentrations as shown in the table below were prepared using a standard triolein solution (250 mg/dl) and a glycerol solution.

| | Sample No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Triolein (mg/dl) | 0 | 50 | 100 | 150 | 200 | 250 | 0 | 50 | 100 | 150 | 200 | 250 |
| Glycerol (mg/dl) | 0 | 0 | 0 | 0 | 0 | 0 | 5 | 5 | 5 | 5 | 5 | 5 |

To 1.5 ml of 50 mM Tris-HCl buffer solution (pH 7.8) containing 0.36 u/ml glycerol kinase, 2 mM GSH, 0.2 mM MgCl$_2$, 1 u/ml iCDH, 5 mM isocitric acid, 5 u/ml glycerol-3-phosphate oxidase, 0.5 mM NADPH, 0.5 u/ml GR, 1 u/ml GSHPOD and 0.002 mM ATP, was added 20 µl each of the test samples prepared above, and the mixture was allowed to stand at 37° C. for ten minutes. 50 mM Tris-HCl buffer solution (pH 7.8) containing 10 u/ml lipoprotein lipase and 20 mM EDTA-4Na was then added (1.5 ml each), the mixture was allowed to stand at 37° C. for 15 minutes and then at room temperature for about ten minutes, and the absorbance at 340 nm was measured. The result obtained is summarized in the table below.

| | Sample No. | | | | | |
|---|---|---|---|---|---|---|
| | 1 | 2 | 3 | 4 | 5 | 6 |
| Measurements ($\Delta A_{340}$ nm) | 0.002 | 0.022 | 0.047 | 0.074 | 0.093 | 0.118 |
| Triolein (mg/dl) | 0.0 | 43.1 | 107.8 | 155.2 | 196.2 | 250.2 |

-continued

| | Sample No. | | | | | |
|---|---|---|---|---|---|---|
| | 7 | 8 | 9 | 10 | 11 | 12 |
| Measurements ($\Delta A_{340}$ nm) | 0.002 | 0.025 | 0.050 | 0.070 | 0.091 | 0.116 |
| Triolein (mg/dl) | 0.0 | 49.6 | 103.5 | 146.6 | 191.9 | 245.8 |

The amount of glycerol was calculated from the value of $\Delta A_{340nm}$ from which the reagent blanks had been subtracted, assuming the molecular weight of triolein 885.45.

It was thus demonstrated that the amount of triolein can be measured with no effect of glycerol added.

Effects Achieved by the Invention

The method of this invention comprises a new step of eliminating endogenous substances in the AND(P)H regeneration system using iCDH, which is followed by measurement of the amount of hydrogen peroxide formed, and hence has outstanding advantages over the conventional methods as described below. This invention provides a new method of analyzing biochemical substances using hydrogen peroxide in the detection system, wherein enzymes or enzyme groups, or substrates or substrate groups, required for the reaction to generate hydrogen peroxide are admixed to a test sample, together with glutathione peroxidase, glutathione reductase, isocitric acid, AND(P)H, metal ions and isocitrate dehydrogenase, thereby consuming endogenous substances contained in body fluid that participate in the reaction system to measure the biochemical substances (substrates, enzymes, etc.) being analyzed and hence produce measurement errors; a metal chelating agent is then added to terminate the reaction of isocitrate dehydrogenase; simultaneously or thereafter an enzyme or substrate that generates hydrogen peroxide as reaction product is added, followed by measurement of the amount of hydrogen peroxide thus formed. The factors interfering with the measurment can thus be removed, ensuring correct measurement. Since living bodies contain a variety of such interfering factors, the method of this invention is particularly useful for the quantitative analysis of biochemical substances in samples taken from organisms, and can be advantageously applied to various types of diagnosis.

This method also provides a new type of reagent whereby oxidase is allowed to act upon substances contained in a test sample or substances formed by specific reactions, thus converting all the enzymes or substrates participating in the reaction system into hydrogen peroxide.

Such outstanding features of the method of this invention are based on the facts that decrease in the amount of AND(P)H with definite molar extinction coefficient is used for measurement, that the measurement is little affected by the color of test samples, pH of the reaction system and other factors, and that the coupled reactions of iCDH and GR are utilized to allow regeneration of reduced-form glutathione and AND(P)H, thus avoiding background fluctuations caused by consumption of the endogenous interfering substances. The method of this invention is also applicable to automatic analyzers through the end-point and rate assay, opening the way to rapid, simple and correct measurement.

What is claimed is:

1. An enzyme assay for the quantitative analysis of a biochemical substance which, when subjected to a predetermined enzyme or substrate, undergoes a reaction which, either directly or indirectly after adding one or more secondary enzymes or substrates, yields hydrogen peroxide as a reaction product, comprising:

adding to a test sample glutathione (GSH), glutathione peroxidase (GSHPOD), glutathione reductase (GR), NADPH or NADH, isocitric acid, metal ions, isocitrate dehydrogenase, and any of said one or more secondary enzymes or substrates, thereby consuming any endogenous substances which may generate hydrogen peroxide upon reaction with any of said added substances, or that would otherwise eventuate in the oxidation of NADPH or NADH to NADP+ or NAD+, and regenerating NADPH or NADH at the same time;

inactivating the isocitrate dehydrogenase;

adding, simultaneously with or after said inactivating step, said predetermine enzyme or substrate that generates hydrogen peroxide as reaction product when reacting with the biological substance directly or indirectly after further reaction with said one or more secondary enzymes or substrates, whereby any formed hydrogen peroxide will be subjected to the action of the GSHPOD in the presence of the GSH to produce oxidized glutathione (GSSG) and any formed GSSG will be subjected to the action of the GR to produce NADP+ or NAD+ from the NADPH or NADH previously added or regenerated; and measuring at 340 nm any decrease of the NADPH or NADH.

2. An assay for the quantitative analysis of a biochemical substance which, when subjected to a predetermined enzyme or substrate, either directly or indirectly after being subjected to one or more secondary enzymes or substrates, undergoes a reaction yielding hydrogen peroxide as a reaction product, comprising:

(a) adding to a sample suspected of containing the biochemical substance being assayed, under conditions which permit the reactions to proceed, (1) a sufficient amount of glutathione (GSH) and glutathione peroxidase (GSHPOD) to react with all of the hydrogen peroxide to yield oxidized glutathione (GSSG), (2) a sufficient amount of NADH or NADPH and glutathione reductase (GR) to react with all of the GSSG to yield GSH and NAD+ or NADP+, and (3) a sufficient amount of any secondary enzyme or substrate which may be necessary, in conjunction with said predetermined enzyme or substrate, to cause all of the biochemical substance in the sample to yield hydrogen peroxide as a reaction product;

(b) simultaneously with or after said adding step, adding a sufficient amount of said predetermined enzyme or substrate to cause, either alone or in conjunction with any added secondary enzyme or substrate, all of the biochemical substance in the sample to yield hydrogen peroxide as a reaction product; and (c) measuring at 340 nm any decrease of the added NADH or NADPH, said decrease being proportional to the amount of biochemical in the sample.

3. An assay in accordance with claim 2, whereby any endogenous substances in the sample which may generate hydrogen peroxide upon reaction with any of said substances added in step (a), or would otherwise eventuate in the oxidation of NADPH or NADH to NADP+ or NAD+, are consumed, wherein said step (b) is after said step (a), further including the steps of:

(d) prior to said step (b), adding a sufficient amount of isocitric acid, metal ions and isocitrate dehydrogenase to react with any NAD+ or NADP+ generated by reaction of any said endogenous material in the sample with the substance added in step (a), to regenerate any NADH or NADPH which has been consumed; and (e) after said step (d) but not later than step (b), inactivating the isocitrate dehydrogenase.

4. An assay in accordance with claim 3, wherein said step (e) comprises adding a sufficient amount of a chelating agent.

5. An assay in accordance with claim 1, wherein said inactivating step comprises adding a sufficient amount of a chelating agent.

6. An enzyme assay for the quantitative analysis of a biochemical substance which, when subjected to a predetermined enzyme or substrate, undergoes a reaction which, either directly or indirectly after adding one or more secondary enzymes or substrates, yields hydrogen peroxide as a reaction product, comprising:

adding to a test sample glutathione (GSH), glutathione peroxidase (GSHPOD), glutathione reductase (GR), NADPH, isocitric acid, metal ions, isocitrate dehydrogenase and said one more secondary enzymes or substrates, thereby consuming any endogenous substances which may generate hydrogen peroxide upon reaction with any of said added substances, or would otherwise eventuate in the oxidation of NADPH to NADP+ and regenerating NADPH at the same time;

inactivating the isocitrate dehydrogenase;

adding, simultaneously with or after said inactivating step, said predetermined enzyme or substrate that generates hydrogen peroxide as reaction product when reacting with the biological substance directly or indirectly after further reaction with said one or more secondary enzymes or substrates, whereby any formed hydrogen peroxide will be subjected to the action of the GSHPOD in the presence of the GSH to produce oxidized glutathione (GSSG) and any formed GSSG will be subjected to the action of the GR to produce NADP+ from the NADPH previously added or regenerated; and measuring at 340 nm any decrease of the NADPH.

7. An assay for the quantitative analysis of a biochemical substance which, when subjected to a predetermined enzyme or substrate, either directly or indirectly after being subjected to one or more secondary enzymes or substrates, undergoes a reaction yielding hydrogen peroxide as a reaction product, comprising:

(a) adding to a sample suspected of containing the biochemical substance being assayed, under conditions which permit the reactions to proceed, (1) a sufficient amount of glutathione (GSH) and glutathione peroxidase (GSHPOD) to react with all of the hydrogen peroxide to yield oxidized glutathione (GSSG), (2) a sufficient amount of NADPH and glutathione reductase (GR) to react with all of the GSSG to yield GSH and NADP+, and (3) a sufficient amount of any secondary enzyme or substrate which may be necessary, in conjunction with said predetermined enzyme or substrate, to cause all of the biochemical substance in the sample to yield hydrogen peroxide as a reaction product;

(b) simultaneously with or after said adding step, adding a sufficient amount of said predetermined enzyme or substrate to cause, either alone or in conjunction with any added secondary enzyme or substrate, all of the biochemical substance in the sample to yield hydrogen peroxide as a reaction product; and (c) measuring at 340 nm any decrease of the added NADPH, said decrease being proportional to the amount of biochemical substance in the sample.

8. An assay in accordance with claim 7, whereby any endogenous substances in the sample which may generate hydrogen peroxide upon reaction with any of said substances added in step (a), or would otherwise eventuate in the oxodation of NADPH to NADP+ are consumed, wherein said step (b) is after said step (a), further including the steps of:

(d) prior to said step (b), adding a sufficient amount of isocitric acid, metal ions and isocitrate dehydrogenase to react with any NADP+ generated by reaction of any said endogenous material in the sample with the substance added in step (a), to regenerate any NADPH which has been consumed; and (e) after said step (d) but not later than said step (b), inactivating the isocitrate dehydrogenase.

9. An assay in accordance with claim 8, wherein said step (e) comprises adding a sufficient amount of a chelating agent.

10. An assay in accordance with claim 6, wherein said inactivating step comprises adding a sufficient amount of a chelating agent.

* * * * *